United States Patent
Smith et al.

(10) Patent No.: US 10,899,986 B2
(45) Date of Patent: *Jan. 26, 2021

(54) SUBSTITUTED MANNICH BASE FUEL ADDITIVES, COMPOSITIONS, AND METHODS

(71) Applicant: Evonik Operations GmbH, Essen (DE)

(72) Inventors: Buford Brian Smith, Evansville, WI (US); Gamini Ananda Vedage, Bethlehem, PA (US)

(73) Assignee: Evonik Operations GmbH, Essen (DE)

( * ) Notice: Subject to any disclaimer, the term of this patent is extended or adjusted under 35 U.S.C. 154(b) by 15 days.

This patent is subject to a terminal disclaimer.

(21) Appl. No.: 16/324,203

(22) PCT Filed: Aug. 25, 2017

(86) PCT No.: PCT/US2017/048625
§ 371 (c)(1),
(2) Date: Feb. 8, 2019

(87) PCT Pub. No.: WO2018/039563
PCT Pub. Date: Mar. 1, 2018

(65) Prior Publication Data
US 2019/0169515 A1   Jun. 6, 2019

Related U.S. Application Data

(60) Provisional application No. 62/379,314, filed on Aug. 25, 2016.

(51) Int. Cl.
| | | |
|---|---|---|
| C10L 1/236 | (2006.01) | |
| C10L 10/06 | (2006.01) | |
| C10L 10/04 | (2006.01) | |
| C08F 132/06 | (2006.01) | |
| C08C 19/22 | (2006.01) | |
| C10L 1/14 | (2006.01) | |
| C07C 253/30 | (2006.01) | |
| C10L 1/238 | (2006.01) | |
| C07C 209/48 | (2006.01) | |
| C10L 1/198 | (2006.01) | |
| C10L 1/16 | (2006.01) | |

(52) U.S. Cl.
CPC ............ *C10L 1/236* (2013.01); *C07C 209/48* (2013.01); *C07C 253/30* (2013.01); *C08C 19/22* (2013.01); *C08F 132/06* (2013.01); *C10L 1/143* (2013.01); *C10L 1/238* (2013.01); *C10L 10/04* (2013.01); *C10L 10/06* (2013.01); *C10L 1/1616* (2013.01); *C10L 1/1985* (2013.01); *C10L 2200/0423* (2013.01); *C10L 2270/023* (2013.01)

(58) Field of Classification Search
CPC combination set(s) only.
See application file for complete search history.

(56) References Cited

U.S. PATENT DOCUMENTS

| | | | |
|---|---|---|---|
| 4,231,759 A | 11/1980 | Udelhofen et al. | |
| 4,242,212 A * | 12/1980 | Hanson | C10L 1/221 508/558 |
| 4,463,157 A | 7/1984 | Kersten et al. | |
| 5,280,091 A | 1/1994 | Dubowik et al. | |
| 5,663,457 A | 9/1997 | Kolp | |
| 5,876,468 A | 3/1999 | Moreton | |
| 6,015,863 A | 1/2000 | Mike et al. | |
| 7,491,248 B2 | 2/2009 | Colucci et al. | |
| 2013/0305596 A1* | 11/2013 | Amblard | C10L 1/19 44/411 |

FOREIGN PATENT DOCUMENTS

| | | |
|---|---|---|
| CN | 1230561 A | 10/1999 |
| DE | 2904314 A1 | 8/1980 |
| EP | 0831141 A1 | 3/1998 |

OTHER PUBLICATIONS

PCT International Search Report dated Nov. 20, 2017 corresponding PCT Application No. PCT/US2017048625 filed Aug. 25, 2017 (6 pages).

* cited by examiner

*Primary Examiner* — Ellen M McAvoy
*Assistant Examiner* — Chantel L Graham
(74) *Attorney, Agent, or Firm* — Andrew H. Chung; Linda S. Li; Jason S. Ngui

(57) ABSTRACT

Mannich base compositions include the reaction products of (1) an amine component including at least one multifunctional amine of structure (1):

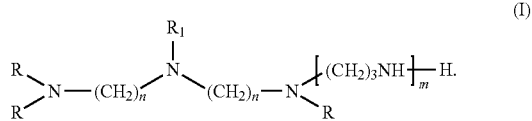

wherein each R is independently H or $CH_2CH_2CH_2NH_2$; $R_1$ is H, $CH_2CH_2CH_2NH_2$, C1-C21 alkyl, or C2-C21 alkenyl; n is 2; and m is 1 or 2, with (2) an alkyl substituted hydroxyaromatic compound, and (3) and aldehyde. The Mannich base compositions are useful for fuel additives and other articles. Additive compositions, fuel additives, fuel compositions and methods for reducing deposit formations in a fuel system are also disclosed.

16 Claims, No Drawings

SUBSTITUTED MANNICH BASE FUEL ADDITIVES, COMPOSITIONS, AND METHODS

This Application is a § 371 national stage of PCT International Application No. PCT/US2017/048625, filed Aug. 25, 2017, which claims the benefit of U.S. Application No. 62/379,314, filed Aug. 25, 2016, the contents of each of which are hereby incorporated by reference in their entirety into this application.

BACKGROUND OF THE INVENTION

The present disclosure is directed to a composition and a method for forming Mannich bases from polyalkylene polyamines. More specifically, the present disclosure is directed to Mannich base compositions formed from polyalkylene polyamines.

Mannich bases are utilized extensively in many markets including agricultural chemicals, medicinal compounds, soaps, detergents, automotive fuel and lube treatments, and epoxy coatings. They comprise the reaction products of hydroxyaromatic (substituted or unsubstituted) compounds with aldehydes and amines of various sorts.

An alkylated hydroxyaromatic compound is first prepared by the acid-catalyzed reaction of an oligomeric or polymeric alkenyl group. Usually polyisobutylene (PIB) is used, although other alkenyl substituents may be used as well. Commercial standard or high vinylidene PIB is reacted with common hydroxyaromatics, such as phenol or o-cresol, in making the intermediate which is then reacted with an aldehyde and an amine or ammonia to give the condensation product.

Polyethylene polyamines, such as diethylene triamine (DETA), triethylene tetramine (TETA), tetraethylene pentamine (TEPA), pentaethylene hexamine (PEHA), hexaethylene heptamine (HEHA), and the like, are often employed in the preparation of Mannich base fuel and lube detergents. In this actual commercial practice, a polyethylene polyamine commonly employed is TEPA (U.S. Pat. No. 4,231,759) to provide the Mannich base dispersant/detergent which can be used alone or as a multicomponent blend with alkenyl succinimides and potentially polyether amine detergents (U.S. Pat. No. 7,491,248).

Polyethylene polyamines are conventionally manufactured from the reaction of ammonia with either ethylene dichloride or ethanolamine. As new manufacturing assets are built to produce polyethylene polyamines, there is a tendency to favor the ethanolamine process, as it is less corrosive to the manufacturing equipment, and hence, more economical. Unfortunately, the ethanolamine process generally produces a lower yield of higher polyethylene polyamines, such as TETA and TEPA, than the ethylene dichloride process, and therefore prices for TETA and TEPA are increasing relative to the prices for other polyethylene polyamines. Furthermore, the demand for higher polyethylene polyamines, especially TEPA, is increasing. There is therefore a need for more economical alternatives to TETA, and especially TEPA, in the manufacture of Mannich base fuel and lube detergents.

Additionally, TEPA is often produced as a mixture of polyamines including cyclic pentamines like 1-(2-aminoethyl)-4-[(2-aminoethyl)amino]ethyl]-piperazine) and 1-[2-[[2-[(2-aminoethyl)amino]ethyl]-amino]ethyl]-piperazine) which may engender reactivity issues due to their steric hindrance. A non-cyclic amine reduces the issue with steric hindrances and reduces or eliminates reactivity issues.

The disclosure of the previously identified patents is hereby incorporated by reference.

A unique Mannich base reaction product based on an alkyl-substituted hydroxyaromatic compound, an aldehyde, and a non-cyclic polyalkylene polyamine is desirable in the art. This product finds utility as a fuel dispersant/detergent.

BRIEF SUMMARY OF THE INVENTION

Embodiments according to the present disclosure include substituted Mannich base reaction products and methods for fuel detergent additives. These substituted Mannich base reaction products compositions, according to the present disclosure, provide useful performance as fuel detergents.

An exemplary embodiment of the present disclosure includes a substituted Mannich detergent composition including the reaction product of (1) an amine component including at least one multifunctional amine of structure (I):

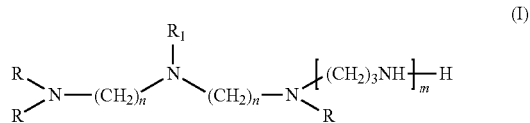

wherein each R is independently H or $CH_2CH_2CH_2NH_2$; $R_1$ is H, $CH_2CH_2CH_2NH_2$, C1-C21 alkyl, or C2-C21 alkenyl; n is 2; and m is 1 or 2, with (2) an aldehyde such as formaldehyde or other aldehydes having up to 18 carbons, and (3) an alkyl-substituted hydroxyaromatic compound derived from phenol or cresol alkylated with copolymers of butylene and/or isobutylene and/or propylene, and potentially one or more mono-olefinic co-monomers co-polymerizable therewith.

In one exemplary embodiment, a substituted Mannich detergent composition includes the reaction product of (1) an amine component including at least one multifunctional amine of structure (I):

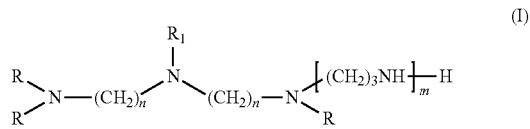

wherein each R is independently H or $CH_2CH_2CH_2NH_2$; $R_1$ is H; n is 2; and m is 1 or 2, with (2) an aldehyde such as formaldehyde or other aldehydes having up to 18 carbons, and (3) an alkyl-substituted hydroxyaromatic compound derived from phenol or cresol alkylated with copolymers of butylene and/or isobutylene and/or propylene, and potentially one or more mono-olefinic co-monomers co-polymerizable therewith.

While the above described amine component approximates a replacement for TEPA, as another exemplary embodiment, an analogous replacement for TETA includes a reaction product of (1) an amine component including at least one multifunctional amine of structure (II):

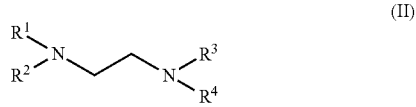

wherein R1-R4 is independently H or CH₂CH₂CH₂NH₂; with (2) an aldehyde such as formaldehyde or other aldehydes having up to 18 carbons, and (3) an alkyl-substituted hydroxyaromatic compound derived from phenol or cresol alkylated with copolymers of butylene and/or isobutylene and/or propylene, and potentially one or more mono-olefinic co-monomers co-polymerizable therewith.

In another exemplary embodiment, there is provided a fuel detergent system or composition containing an amine-aldehyde-alkyl substituted hydroxyaromatic Mannich base composition.

In another exemplary embodiment, there is provided a fuel composition including fuel and the substituted Mannich base reaction fuel additive including the amine-aldehyde-alkyl substituted hydroxyaromatic Mannich base composition according to the present disclosure.

In another exemplary embodiment, a method to reduce deposit formation in a fuel system of an internal combustion engine. The method includes operating the internal combustion system with a fuel composition including fuel and the substituted Mannich base reaction fuel additive including the amine-aldehyde-alkyl substituted hydroxyaromatic Mannich base composition according to the present disclosure.

Other features and advantages of the present disclosure will be apparent from the following more detailed description of the preferred embodiment, taken in conjunction with the accompanying drawings which illustrate, by way of example, the principles of the invention.

DETAILED DESCRIPTION OF THE INVENTION

Provided are amine-aldehyde-alkyl substituted hydroxyaromatic Mannich base reaction compositions and methods for fuel detergent additives. These substituted Mannich base products, according to the present disclosure, provide useful performance as fuel detergents. As another advantage of the present disclosure, these substituted Mannich base compositions, which do not contain triethylenetetramine (TETA) or tetraethylenepentamine (TEPA), nonetheless have physical properties including viscosity, molecular weight and amine hydrogen equivalent weight (HEW) that closely resemble conventional Mannich products derived from triethylenetetramine (TETA) or tetraethylenepentamine (TEPA). Suitable applications include, but are not limited to fuel additives, lubricant additives, and other articles.

As another advantage, the non-cyclic amine structures of the polyamine affords a more complete Mannich reaction to form the substituted Mannich base composition due to non-steric hindrance compared to certain grades of TEPA.

The substituted Mannich base product compositions according to the present disclosure include the reaction products of (1) an amine component including at least one multifunctional amine of structure (I):

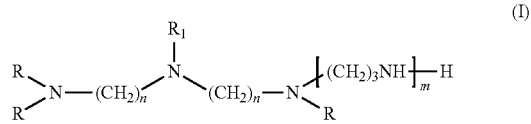
(I)

wherein each R is independently H or CH₂CH₂CH₂NH₂; R₁ is H, CH₂CH₂CH₂NH₂, C1-C21 alkyl, or C2-C21 alkenyl; n is 2; and m is 1 or 2, with (2) an aldehyde such as formaldehyde or other aldehydes having up to 18 carbons, and (3) an alkyl-substituted hydroxyaromatic compound derived from phenol or cresol alkylated with copolymers of butylene and/or isobutylene and/or propylene, and potentially one or more mono-olefinic co-monomers co-polymerizable therewith.

The alkylation of the hydroxyaromatic compound is typically performed in the range of about 50° to about 200° C. using acidic catalysts generally used to promote Friedel-Crafts alkylation such as sulphuric acid, BF3, aluminum phenoxide, methanesulphonic acid and cationic exchange resin. The mole ratio of alkene to hydroxyaromatic is 1:2-3 with the excess hydroxyaromatic being removed by distillation after the reaction often with the aid of a solvent. The condensation reaction among the specified amine(s), the aldehyde, and the alkyl-substituted hydroxyaromatic compound may be conducted at a temperature in the range of about 40° to about 200° C. The reaction may be conducted in bulk (no diluent or solvent) or in a solvent or diluent such as Aromatic 100 or 150 from Exxon Mobil. The amine is typically charged portion-wise to the combination of the other two reagents. Water is evolved and may be removed by direct or azeotropic distillation during the course of the reaction with or without the aid of an inert gas sparge to aid removal. Typically, the Mannich reaction products are formed by reacting the alkyl-substituted hydroxyaromatic compound, the aldehyde and amine in the molar ratio of 1.0:1.0-3.5:0.5-2.0, respectively.

The amine component used to prepare the substituted Mannich base composition includes at least one multifunctional amine of structure (I). In one exemplary embodiment of the present disclosure, R1 is H in structure (I). In another exemplary embodiment, R1 is CH₂CH₂CH₂NH₂. In yet another embodiment, R1 is a substituted or un-substituted benzyl group of C7-C21. In another embodiment, R1 is a C1-C21 alkyl, or C2-C21 alkenyl group derived from the reaction of mono-glycidyl ether of corresponding alcohol or phenol with the secondary amine NH before R1 is attached.

The multifunctional amines of structure (I) of the present disclosure include, but are not limited to, N-3-aminopropyl diethylenetriamine (N4); N-3-aminopropyl-[N'-3-[N-3-aminopropyl]aminopropyl]diethylenetriamine (N6); N,N'-bis(3-aminopropyl)diethylenetriamine (N5); N,N-bis(3-aminopropyl)diethylenetriamine (N5); N,N,N'-tris(3-aminopropyl)diethylenetriamine (N6); N,N',N'''-tris(3-aminopropyl)diethylenetriamine (N6); N,N,N',N'-tetrakis(3-aminopropyl)diethylenetriamine (N7); N,N-bis(3-aminopropyl)-[N'-3-[N-3-aminopropyl]aminopropyl]-[N'-3-aminopropyl]diethylenetriamine (N8); N-3-aminopropyl-[N'-3-[N-3-aminopropyl]aminopropyl]-[N'-3-aminopropyl] diethylenetriamine (N7); These multifunctional amines may be prepared by the Michael reaction of diethylenetriamine with acrylonitrile, followed by hydrogenation over metal catalysts as is well known to those skilled in the art. It is also known to those skilled in the art, the multifunctional amines comprise a mixture of amines represented by structure (I) having 4 nitrogen atoms (N4), having 5 nitrogen atoms (N5), and having at least 6 nitrogen atoms (N6 and higher amine). Each of amine N4, N5, N6 and higher amines in the mixture may contain more than one structural isomers. A representative reaction scheme is shown below.

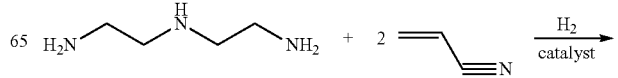

-continued

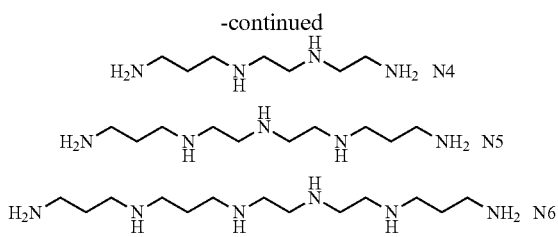

A suitable multifunctional amine represented by structure (I) for use as the amine component to prepare Mannich base products is N,N'-bis(3-aminopropyl)diethylenetriamine (N5). A particularly suitable multifunctional amine represented by structure (I) is a mixture comprising in a parts-by-weight (pbw) ratio of 0 to 50 pbw amine having 4 nitrogen atoms (N4), 40 to 95 pbw amine having 5 nitrogen atoms (N5), and 0 to 50 pbw amine having at least 6 nitrogen atoms (N6 and higher amine), or a suitable ratio of 0 to 30 pbw amine having 4 nitrogen atoms (N4), 40 to 95 pbw amine having 5 nitrogen atoms (N5), and 0 to 50 pbw amine having at least 6 nitrogen atoms (N6 and higher amine), or a suitable ratio of 0 to 20 pbw amine having 4 nitrogen atoms (N4), 50 to 95 pbw amine having 5 nitrogen atoms (N5), and 0 to 40 pbw amine having at least 6 nitrogen atoms (N6 and higher amine), or a suitable ratio of 0 to 20 pbw amine having 4 nitrogen atoms (N4), 50 to 90 pbw amine having 5 nitrogen atoms (N5), and 3 to 35 pbw amine having at least 6 nitrogen atoms (N6 and higher amine), or a suitable ratio of 1 to 15 pbw amine having 4 nitrogen atoms (N4), 50 to 90 pbw amine having 5 nitrogen atoms (N5), and 5 to 35 pbw amine having at least 6 nitrogen atoms (N6 and higher amine). Such a mixture may be prepared by the reaction sequence described above for making the multifunctional amine without the need to conduct a distillation or other process of separation, except for the optional removal of low molecular weight side products of the reaction which are more volatile than N-3-aminopropyldiethylenetriamine. It will be recognized by those skilled in the art that small quantities of other products of hydrogenation may be present in the mixture.

While the above described amine component (I) approximates a replacement for TEPA, an analogous replacement for TETA includes a reaction product of (1) an amine component including at least one multifunctional amine of structure (II):

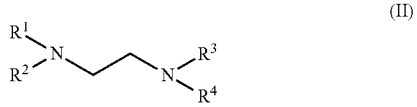

(II)

The Mannich Base reaction product composition according to the present disclosure includes the reaction products of (1) an amine component including at least one multifunctional amine of structure (II) wherein each R is independently H or $CH_2CH_2CH_2NH_2$; with (2) an aldehyde such as formaldehyde or other aldehydes having up to 18 carbons, and (3) an alkyl-substituted hydroxyaromatic compound derived from phenol or cresol alkylated with copolymers of butylene and/or isobutylene and/or propylene, and potentially one or more mono-olefinic co-monomers co-polymerizable therewith.

The amine component (II) used to prepare the Mannich Base reaction product includes at least one multifunctional amine of structure (II). In one exemplary embodiment of the present disclosure, R1 and R3 is H in structure (II) while R2 and R4 are $CH_2CH_2CH_2NH_2$. In another exemplary embodiment, R1 is H and R2-R4 are $CH_2CH_2CH_2NH_2$. In another exemplary embodiment, one of the R groups being $CH_2CH_2CH_2NH_2$ is derivatized with a substituted or un-substituted benzyl group of C7-C21. In yet another embodiment, one of the R groups being $CH_2CH_2CH_2NH_2$ is derivatized with a C1-C21 alkyl, or C2-C21 alkenyl group arising from the reaction of mono-glycidyl ether of corresponding alcohol or phenol with the amine.

Representative aldehydes for use in the preparation of the substituted Mannich base composition, according to the present disclosure, include aliphatic aldehydes, such as formaldehyde, acetaldehyde, propionaldehyde, butyraldehyde, valeraldehyde, caproaldehyde, heptaldehyde, stearaldehyde. Aromatic aldehydes which may be used in the reaction include benzaldehyde and salicylaldehyde. Illustrative heterocyclic aldehydes for use herein are furfural and thiophene aldehyde, etc. Also useful in the reaction to form the substituted Mannich base composition are formaldehyde-producing reagents, such as paraformaldehyde, or aqueous formaldehyde solutions, such as formalin. Particularly preferred aldehydes include formaldehyde or formalin.

The substituted Mannich base products require hydroxyaromatic alkylation intermediates in the reaction mixture to form the substituted Mannich base composition. Representative alkyl-substituted hydroxyaromatic compounds that may be used in forming the present Mannich base products are polypropylphenol (formed by alkylating phenol with polypropylene), polybutylphenols (formed by alkylating phenol with polybutenes and/or polyisobutylene), and polybutyl-co-polypropylphenols (formed by alkylating phenol with a copolymer of butylene and/or butylene and propylene). Other similar long-chain alkylphenols may also be used as the alkyl-substituted hydroxyaromatic compound. Examples include phenols alkylated with copolymers of butylene and/or isobutylene and/or propylene, and one or more mono-olefinic co-monomers co-polymerizable therewith (e.g., ethylene, 1-pentene, 1-hexene, 1-octene, 1-decene, etc.) where the copolymer molecule contains at least 50% by weight, of butylene and/or isobutylene and/or propylene units. The co-monomers polymerized with propylene or such butenes may be aliphatic and may also contain non-aliphatic groups, e.g., styrene, o-methylstyrene, p-methylstyrene, divinyl benzene and the like. Thus in any case the resulting polymers and copolymers used in forming the alkyl-substituted hydroxyaromatic compounds are substantially aliphatic hydrocarbon polymers.

In one embodiment herein, polybutylphenol (formed by alkylating phenol with polybutylene) is used in forming the substituted Mannich base composition. Unless otherwise specified herein, the term "polybutylene" is used in a generic sense to include polymers made from "pure" or "substantially pure" 1-butene or isobutene, and polymers made from mixtures of two or all three of 1-butene, 2-butene and isobutene. Commercial grades of such polymers may also contain insignificant amounts of other olefins. So-called high reactivity polybutylenes having relatively high proportions of polymer molecules having a terminal vinylidene group, formed by methods such as described, for example, in U.S. Pat. No. 4,152,499 and W. German Offenlegungsschrift 29 04 314, which are incorporated by reference, are also suitable for use in forming the alkyl-substituted hydroxyaromatic compounds.

The alkylation of the hydroxyaromatic compound is typically performed in the presence of an alkylating catalyst at a temperature in the range of about 50° to about 200° C. Acidic catalysts are generally used to promote Friedel-Crafts alkylation. Typical catalysts used in commercial production include sulphuric acid, BF3, aluminum phenoxide, methanesulphonic acid, cationic exchange resin, acidic clays and modified zeolites. U.S. Pat. Nos. 5,663,457 and 8,425,629, which are incorporated by reference, describe methods for the hydroxyaromatic alkylation used to provide an alkylated hydroxyaromatic compound, PIB Phenol, herein used for preparing the substituted Mannich base composition.

The long chain alkyl substituents on the benzene ring of the hydroxyaromatic compound are derived from polyolefin having a number average molecular weight (MW) of from about 250 to about 3000 (preferably from about 500 to about 2100) as determined by gel permeation chromatography (GPC). It is also preferred that the polyolefin used have a polydispersity (weight average molecular weight/number average molecular weight) in the range of about 1 to about 4 (preferably from about 1 to about 2) as determined by GPC.

The substituted Mannich base composition may be made from a long chain alkylphenol. However, other phenolic compounds may be used including high molecular weight alkyl-substituted derivatives of resorcinol, hydroquinone, catechol, hydroxydiphenyl, benzylphenol, phenethylphenol, naphthol, tolylnaphthol, among others. Preferred for the preparation of the substituted Mannich base compositions are the polyalkylphenol and polyalkylcresol reactants, e.g., polypropylphenol, polybutylphenol, polypropylcresol and polybutylcresol, wherein the alkyl group has a number average molecular weight of about 250 to about 2100, while the most preferred alkyl group is a polybutyl group derived from polybutylene having a number average molecular weight in the range of about 250 to about 1500.

The preferred configuration of the alkyl-substituted hydroxyaromatic compound suitable for use in formatting the Mannich base composition is that of a para-substituted mono-alkylphenol or a para-substituted mono-alkyl orthocresol. However, any alkylphenol readily reactive in the Mannich condensation reaction may be employed. Thus, Mannich products made from alkylphenols having only one ring alkyl substituent, or two or more ring alkyl substituents are suitable for use in this disclosure. The long chain alkyl substituents may contain some residual unsaturation, but in general, are substantially saturated alkyl groups.

In another embodiment of the present disclosure, the substituted Mannich base composition further comprises at least one substituted hydroxyaromatic compound. Specific examples of substituted hydroxyaromatic compounds include, but are not limited to, alkyl substituted phenols, dimethylaminomethylphenol, bis(dimethylaminomethyl)phenol, and tris(dimethylaminomethyl)phenol.

In some embodiments according to the present disclosure, the multifunctional amines include a mixture of multifunctional amines. In other embodiments according to the present disclosure, the substituted Mannich base composition is based on a mixture of multifunctional amines of the present disclosure.

If desired, the substituted Mannich composition may be modified by incorporation of other multifunctional amines having two (2) or more active amine hydrogens. Non-limiting examples of multifunctional amines having two (2) or more active amine hydrogens that are within the scope of the present disclosure include, but are not limited to, an aliphatic amine, a cycloaliphatic amine, an aromatic amine, a poly(alkylene oxide) diamine or triamine, a Mannich base derivative of an aliphatic amine, a Mannich base derivative of a cycloaliphatic amine, a Mannich base derivative of an aromatic amine, a polyamide derivative of an aliphatic amine with a fatty acid, a polyamide derivative of a cycloaliphatic amine with a fatty acid, a polyamide derivative of an aromatic amine with a fatty acid, an amidoamine derivative of an aliphatic amine with a fatty acid, an amidoamine derivative of a cycloaliphatic amine with a fatty acid, an amidoamine derivative of an aromatic amine with a fatty acid, an amine adduct derivative of an aliphatic amine with a mono-glycidyl ether, an amine adduct derivative of a cycloaliphatic amine with a mono-glycidyl ether, or an amine adduct derivative of an aromatic amine with a mono-glycidyl ether, or any combination thereof.

Specific examples of multifunctional amines having two (2) or more active amine hydrogens include, but are not limited to, ethylenediamine, diethylenetriamine, triethylenetetramine, tetraethylenepentamine, higher polyethyleneamines, aminoethylpiperazine, meta-xylylenediamine, the various isomers of diamine-cyclohexane, isophorone diamine, 3,3'-dimethyl-4,4'-diaminodicyclohexyl methane, 4,4'-diaminodicyclohexyl methane, 2,4'-diaminodicyclohexyl methane, the mixture of methylene bridged poly (cyclohexyl-aromatic)amines (MBPCAA) described in U.S. Pat. No. 5,280,091, which is incorporated by reference, 1,2-propylenediamine, 1,3-propylenediamine, 1,4-butanediamine, 1,5-pentanediamine, 1,3-pentanediamine, 1,6-hexanediamine, 3,3,5-trimethyl-1,6-hexane-diamine, 3,5,5-trimethyl-1,6-hexanediamine, 2-methyl-1,5-pentanediamine, bis-(3-amino-propyl)amine, N,N'-bis-(3-aminopropyl)-1,2-ethanediamine, N-(3-aminopropyl)-1,2-ethanediamine, 1,2-diaminocyclohexane, 1,3-diaminocyclohexane, 1,4-diamino-cyclohexane, the poly (alkylene oxide)diamines and triamines (such as, for example, JEFFAMINE® D-230, JEFFAMINE® D-400, JEFFAMINE® D-2000, JEFFAMINE® D-4000, JEFFAMINE® T-403, JEFFAMINE® EDR-148, JEFFAMINE® EDR-192, JEFFAMINE® C-346, JEFFAMINE® ED-600, JEFFAMINE® ED-900, JEFFAMINE® ED-2001) and also aminopropylated ethylene glycols, aminopropylated propanediols, aminopropylated butanediols, aminopropylated hexanediols, aminopropylated polyethylene glycols, aminopropylated polypropylene glycols and aminopropylated polybutanediols. JEFFAMINE® is a registered trademark of Huntsman Corporation. The substituted Mannich base composition may be modified by incorporating these polyamines in the condensation reaction with the aldehyde and substituted hydroxyaromatic compound.

Other suitable ingredients for inclusion in the reaction composition of the present disclosure include polyamines, such as, aliphatic diamine having one primary or secondary amino group and at least one tertiary amino group in the molecule. Examples of suitable polyamines include, but are not limited to, N,N,N",N"-tetraalkyldialkylenetriamines (two terminal tertiary amino groups and one central secondary amino group), N,N,N',N"-tetraalkyltrialkylenetetramines (one terminal tertiary amino group, two internal tertiary amino groups and one terminal primary amino group), N,N,N',N",N'''-pentaalkyltrialkylenetetramines (one terminal tertiary amino group, two internal tertiary amino groups and one terminal secondary amino group), N,N-dihydroxyalkyl-alpha, omega-alkylenediamines (one terminal tertiary amino group and one terminal primary amino group), N,N,N'-trihydroxyalkyl-alpha, omega-alkylenediamines (one terminal tertiary amino group and one terminal secondary amino group), tris(dialkylaminoalkyl)aminoalkylmethanes (three terminal tertiary amino groups and one terminal primary amino group), and similar compounds, wherein the alkyl groups are the same or different and typically contain no more than about 12 carbon atoms each, and which, for example, contain from 1 to 4 carbon atoms each. In an aspect, these alkyl groups may be methyl and/or ethyl groups. In another aspect, polyamine reactants may be N,N-dialkyl-alpha, omega-alkylenediamine, such as those having from 3 to about 6 carbon atoms in the alkylene group and from 1 to about 12 carbon atoms in each of the alkyl groups, which, for example, may be the same but which may be different. In an aspect, N,N-dimethyl-1,3-propanediamine and N-methyl piperazine may be used.

The substituted Mannich base composition may be modified by incorporating these amines in the reaction mixture to form the substituted Mannich base composition. It is then necessary to account for the differences in the molecular weight of the various amines to attain the proper ratio of equivalents of amine/polyamine to equivalents of alkylated hydroxyaromatic compound and aldehyde. As with a reaction situation that involves only the exemplary claimed amine the mole ratio of the alkylated hydroxyaromatic compound to aldehyde to all amines for the Mannich reaction may be 0.5-1:0.5-3.5:0.5-2.0, and in other instances may be 0.7-1:0.7-1:0.7-1, and 0.9-1:0.9-1:0.9-1. These amines may be incorporated at levels up to 75% replacement level of the exemplarily claimed amines.

In one exemplary embodiment, the present disclosure provides a Mannich base composition comprising the contact product of: (i) a substituted Mannich base comprising the reaction products of (1) an amine component including at least one multifunctional amine of structure (I) and/or (II) and (2) an aldehyde and (3) a substituted hydroxyaromatic compound; and (ii) at least one additional multifunctional amine having three or more active amine hydrogens or an amine having at least one primary and/or secondary amine as well as at least one tertiary amine.

The term "contact product" is used herein to describe compositions wherein the components are contacted together in any order, in any manner, and for any length of time. For example, the components may be contacted by blending or mixing. Further, contacting of any component may occur in the presence or absence of any other component of the compositions or formulations described herein. Further still, two or more of the components of the contact product may react to form other components composing the composition. Combining additional materials or components may be done by any method known to one of skill in the art.

It is also possible to modify the substituted Mannich base of the present disclosure by reacting up to 50% of the amine hydrogens with mono-functional epoxides. This is a practice known as "adduction". Styrene oxide, cyclohexene oxide, and the glycidyl ethers of phenol, the cresols, tert-butylphenol and other alkyl phenols, butanol, 2-ethylhexanol, and C8 to C14 alcohols and the like are useful. Hydrogenation of the alkenyl substituent unsaturation also may be done.

Substituted Mannich base compositions, in accordance with the present disclosure, may further comprise at least one multifunctional amine. Multifunctional amine, as used herein, describes compounds with amine functionality and which contain three (3) or more active amine hydrogens.

Non-limiting examples of multifunctional amines having three (3) or more active amine hydrogens that are within the scope of the present disclosure include, but are not limited to, an aliphatic amine, a cycloaliphatic amine, an aromatic amine, a poly(alkylene oxide) diamine or triamine, another Mannich base derivative of an aliphatic amine, another Mannich base derivative of a cycloaliphatic amine, another Mannich base derivative of an aromatic amine, a polyamide derivative of an aliphatic amine with a fatty acid, a polyamide derivative of a cycloaliphatic amine with a fatty acid, a polyamide derivative of an aromatic amine with a fatty acid, an amidoamine derivative of an aliphatic amine with a fatty acid, an amidoamine derivative of a cycloaliphatic amine with a fatty acid, an amidoamine derivative of an aromatic amine with a fatty acid, an amine adduct derivative of an aliphatic amine with a glycidyl ether, an amine adduct derivative of a cycloaliphatic amine with a glycidyl ether, or an amine adduct derivative of an aromatic amine with a glycidyl ether, and the like, or any combination thereof.

The substituted Mannich reaction product of the present disclosure may be prepared from the PIB alkylated hydroxyaromatic compound, aldehyde and amine, as described hereinabove. The mole ratio of the alkylated hydroxyaromatic compound to aldehyde to amine for the Mannich reaction may be 0.5-1:0.5-3.5:0.5-2.0, and in other instances may be 0.7-1:0.7-1:0.7-1, and 0.9-1:0.9-1:0.9-1. The reactants may be combined in any sequence that results in formation of a substituted Mannich reaction product. In an embodiment according to the present disclosure, the amine is added to a mixture of the alkylated hydroxyaromatic compound and aldehyde. A diluent, as described above for the alkylation reaction of the hydroxyaromatic compound and PIB, may be present during the reaction to form a substituted Mannich reaction product. In an embodiment according to the present disclosure, the diluent is a high boiling aliphatic kerosene, a high boiling aromatic naphtha, xylenes or toluene. The diluent may be present in the Mannich reaction mixture and substituted Mannich reaction product at 5 to 95% by weight, and in other instances at 10 to 70% by weight, and 15 to 45% by weight. The Mannich reaction may be run at 50° to 200° C., and in other instances at 70° to 175° C., and at 90° to 150° C. Procedures to prepare a Mannich reaction product are well known and include the procedures described in U.S. Pat. No. 5,876,468, which is incorporated by reference, and in the preparative example herein below.

In one embodiment, the substituted Mannich reaction product formed from the reaction mixture of the multifunctional amine of structure (I) and/or (II), the aldehyde, and the alkyl-substituted hydroxyaromatic compound is an additive composition. Depending on the application or utility of the additive composition, the additive composition may further comprise one or more additional components. An additive composition for use in a lubricant may further comprise a diluent and/or one or more performance additives. The diluent may be a lubricating oil, a solvent, or a mixture thereof. The lubricating oil may be a mineral oil from refining of petroleum, a synthetic oil to include a poly(alpha-olefin) or an ester of a carboxylic acid, or a mixture thereof. The solvent may be an aliphatic hydrocarbon, an aromatic hydrocarbon, an oxygen containing compound to include an alcohol, water, or a mixture thereof. Performance additives for a lubricant may include metal containing detergents, nitrogen containing dispersants, wear and oxidation and corrosion inhibitors, and various surfactants. An additive composition for use in a fuel may further comprise a diluent and/or one or more performance additives, as described herein below, for a fuel additive concentrate composition.

A fuel additive concentrate composition of the present disclosure for an internal combustion engine comprises a solvent, the additive composition comprising the substituted Mannich reaction product of this disclosure, and optionally one or more additional fuel additives. The solvent and optional fuel additive or additives that are present in the concentrate composition will largely depend on the type of internal combustion engine that the concentrate composition is to be used in. The solvent may be an aliphatic hydrocarbon, an aromatic hydrocarbon, a glycol ether, an alcohol, or a mixture thereof. The solvent, for example, may include an aromatic naphtha, an aliphatic kerosene, toluene, xylenes, aliphatic alcohols having 1 to 10 carbon atoms, and mixtures thereof. The solvent is normally present in the concentrate composition in an amount to provide a concentrate composition that is homogeneous and sufficiently fluid for transferring and handling. The solvent may be present in the concentrate composition at 5 to 90% by weight, and in other instances at 10 to 70% by weight, and at 15 to 50% by weight. Carrier fluids, such as those described in U.S. Pat. No. 8,425,629, which is incorporated by reference, may also be employed. Additional fuel additives commonly used in gasoline fuel compositions may include an anti-knock additive, such as lead and cyclopentadienyl manganese tricarbonyl compounds, and a valve seat recession additive, such as alkali metal sulfosuccinate salts. Additional fuel additives commonly used in diesel fuel compositions may include a cetane improver, such as organic nitrate and nitrite compounds, a cold flow improver, such as ethylene-vinyl acetate copolymers, smoke suppressants, and antifoaming agents, such as silicone fluids. Additional fuel additives commonly used in both diesel and gasoline fuel compositions may include antioxidants, such as hindered phenols, supplemental detergents, such as succinimides and hydrocarbyl substituted amines and polyetheramines, corrosion inhibitors, such as alkenylsuccinic acids, antistatic agents, biocides, demulsifiers, fluidizers, such as mineral oils and polyethers and polyetheramines, and lubricity agents, such as tall oil fatty acids. Fuel additives will generally be present in a concentrate composition and fuel composition in an amount that improves performance based on several factors to include engine type, type of engine service conditions, and fuel quality. The substituted Mannich reaction product of the present disclosure may be present in the concentrate composition at 5 to 90% by weight, and in other instances at 7 to 70% by weight, and at 9 to 50% by weight. The additional fuel additive or additives may each be present in the concentrate composition depending on its or their function at 0.01 to 90% by weight, and in other instances at 0.01 to 70% by weight, and at 0.01 to 50% by weight.

A fuel composition of the present disclosure for an internal combustion engine comprises a major amount of a fuel and a minor amount of the above described additive composition that comprises the substituted Mannich reaction product of this disclosure. In another embodiment of this disclosure a fuel composition for an internal combustion engine comprises a major amount of a fuel and a minor amount of the above described fuel additive concentrate composition that comprises solvent, additive composition comprising the substituted Mannich reaction product of the disclosure, and optionally one or more additional fuel additives. The fuel may be a normally liquid fuel. The normally liquid fuel may be a hydrocarbon fuel, a nonhydrocarbon fuel, or a mixture thereof. The hydrocarbon fuel may be a petroleum distillate to include a gasoline as defined by ASTM specification D4814 or a diesel fuel as defined by ASTM specification D975. The hydrocarbon fuel may be a hydrocarbon prepared by a gas to liquid process to include, for example, hydrocarbons prepared by a process, such as a Fischer-Tropsch Process. The nonhydrocarbon fuel may be an oxygen-containing composition, often referred to as an oxygenate, to include alcohols, ethers, ketones, esters of carboxylic acids, nitroalkanes, and mixtures thereof. The nonhydrocarbon fuel, for example, may include methanol, ethanol, methyl t-butyl ether, nitromethane, and transesterified oils from plants and animals, such as rapeseed methyl ester and soybean methyl ester. Mixtures of hydrocarbon and nonhydrocarbon fuels may include gasoline and methanol and/or ethanol, diesel fuel and ethanol, and diesel fuel and a transesterified plant oil, such as rapeseed methyl ester. In an embodiment of the disclosure the fuel is an emulsion of water in a hydrocarbon fuel, a nonhydrocarbon fuel, or a mixture thereof. The Mannich reaction product of the present disclosure may be present in the fuel composition at 10 to 1,000 ppm (parts per million) by weight, and in other instances may be present at 50 to 800 ppm by wt., 65 to 700 ppm by weight, 80 to 500 ppm by weight, and 90 to 250 ppm by weight. Each of the additional fuel additives may be present in the fuel composition depending on their function at 0.01 to 10,000 ppm by wt., and in other instances at 0.01 to 5,000 ppm by wt., and at 0.01 to 1,000 ppm by wt.

The above described fuel additive concentrate composition and fuel composition of the present disclosure may be prepared by admixing or mixing the components of the composition at ambient to elevated temperatures generally up to 60° C. until the composition is homogeneous or substantially homogenous. The composition may be filtered after it is blended.

A method of the present disclosure to reduce deposit formation in a fuel system of an internal combustion engine comprises operating the engine with the above described fuel composition comprising an additive composition that comprises the substituted Mannich reaction product of the disclosure. In another embodiment of the disclosure the method to reduce deposit formation in the fuel system of an internal combustion engine comprises operating the engine with the above described fuel composition comprising a fuel additive concentrate composition that comprises solvent, additive composition comprising the substituted Mannich reaction product of the disclosure, and optionally one or more additional fuel additives. The fuel composition and method of the present disclosure, which employ a substituted Mannich reaction product derived from conventional and/or high vinylidene PIBs, are effective in reducing deposits in a fuel system of an internal combustion engine.

The disclosure is further illustrated by the following examples, which are not to be construed as imposing limitations to the scope of this disclosure. Various other aspects, embodiments, modifications, and equivalents thereof which, after reading the description herein, may suggest themselves to one of ordinary skill in the art without departing from the spirit of the present disclosure or the scope of the appended claims.

EXAMPLES

Synthesis Examples

Amine value is determined by a Metrohm titrator, and chemical composition of the Mannich base intermediates and products are analyzed by nuclear magnetic resonance (NMR). The NMR experiments are performed at ambient temperature employing the Bruker DRX-400 FT-NMR spectrometer equipped with a 10 mm BBO probe. Quantitative $^{13}$C NMR data is acquired using inverse-gated decoupling, a 45° pulse, and a 6 second relaxation delay. The samples are dissolved in chloroform-d with a relaxation agent. The chemical shift scale was referenced to the solvent peak. The composition of the multifunctional amine represented by Structure (I) was analyzed by gas chromatograph (GC).

Example 1. Synthesis of Multifunctional Amine Represented by Structure (I) and Corresponding Mannich Base Step 1. Cyanoethylation of Diethylenetriamine A 1.8 L Mettler-Toledo RC1 reactor was charged with 240 g diethylenetriamine (2.3 moles) and 55.5 g water (3.1 moles) then sealed. The agitator was started, and the reactor was purged with nitrogen then heated to 70° C. When the temperature was at 70° C., 259.1 g acrylonitrile (4.9 moles) was charged from an Isco pump over 4 hours. The reaction mixture was stirred for 30 minutes at 70° C. after the addition was completed. The product then was cooled to ambient temperature and discharged from the reactor into a bottle. Analysis of a sample by GC showed that the mixture contained 0.7% acrylonitrile, 2.9% monocyanoethylated diethylenetriamine, 82.2% dicyanoethylated diethylenetriamine (mixture of isomers), and 12.8% tricyanoethylated diethylenetriamine (mixture of isomers).

Step 2: Semi-Batch Hydrogenation of Cyanoethylated Diethylenetriamine

A 1.8 L Mettler-Toledo RC1 reactor was charged with 250 g isopropanol, 8 g Raney® cobalt 2724 catalyst, and 20 g 10 wt % aqueous LiOH $H_2O$ solution. The reactor was sealed then purged three times with nitrogen, pressure checked, purged three times with hydrogen then pressurized with hydrogen to 500 psig and heated to 140° C. The agitator speed was set to 1000 rpm. When the reaction mixture was at temperature, the hydrogen pressure was increased to 754 psig. Cyanoethylated diethylenetriamine from step 1 above, 800 g, was charged to the reactor over 2 hours from an Isco pump. After the charge was completed, the reaction mixture was held at temperature and pressure for 3 minutes. The reactor was cooled, vented, purged with nitrogen, and the contents were discharged through a filter. Water, isopropanol solvent, and low molecular weight components were removed by vacuum distillation. The final product contained 2.2% monoaminopropylated diethylenetriamine (N4), 79.1% diaminopropylated diethylenetriamine (N5) (mixture of isomers), and 15.2% triaminopropylated diethylenetriamine (N6) (mixture of isomers) based on GC analysis. The monoaminopropylated component is thus minimized.

Step 3. Synthesis of PIB Phenol

A 1 liter round-bottomed flask was charged with 267 g (0.25 mole) polyisobutene (TPC595 from TPC Group, 1069 mwt) dried Amberlyst 35 (45 g) and subsequently BF3-diethyletherate (32 g) and reacted with 118 g (1.25 mole) of phenol at 25° C. to 70° C. for 24 hours with 133 g toluene as a solvent. After catalyst removal, the volatiles (147 g of solvent and excess phenol) were vacuum stripped to 220° C. under vacuum. The product was 99% alkylated by $^{13}C$ and $^1H$ NMR.

Step 4. Synthesis of Substituted Mannich Base from Product of Steps 1-3

Preparation of Substituted Mannich Base from PIB Phenol—Bis-3(aminopropyl) diethylenetriamine—Formaldehyde (1:1:2.2 and 1:1:3.3)

A 1 liter round-bottomed flask was charged with 149 g (0.063 moles) of a solution of 50% p-polyisobutylene phenol in 50% xylene solvent, together with 11.2 g (0.138 moles) of Formalin (37% in water) and 14 g (0.063 moles) of bis-3(aminopropyl) diethylenetriamine (Step 2 product) is added drop wise over a ten minute period. The mixture was heated and stirred to 125-140° C. for a 3.5 hour period until the requisite amount of water (ca. 8 g) was evolved and collected. The resulting product is filtered over Celite and stripped for 3.5 hr over a range of 90-120° C. and 190-70 torr.

A version using 3.3 equivalents of Formalin 16.8 g (0.21 moles) was also prepared in like manner.

Testing of Mannich Bases

The substituted Mannich base prepared in Step 4 was evaluated for effectiveness as a fuel detergent additive. Mixtures were prepared by combining and mixing the components given in examples below. Testing was performed at Southwest Research Institute (SwRI®) using their benchtop Induction System Deposit test (ISD) for detergency tendencies in gasoline, employing the ISD apparatus and protocols developed at SwRI®.

Gasoline Additive Detergency Tests

The substituted Mannich bases of Step 4 were blended with a carrier fluid Exxal 13 poly (24) propoxylate (prepared by Evonik) and Aromatic 150 Solvent (Exxon-Mobil) with levels of each component being in equal ratios by weight. Blend amounts of this formulation into a standard minimally additized gasoline ranged from 500-2000 ppm. 100 ml of the standard fuel was initially run to "dirty-up" the ISD, then after inspection, 100 ml of the standard fuel is additized with the substituted Mannich Base formulation and run through the same apparatus. Inspection determined the degree of ISD "clean-up" that occurred and illustrates the usefulness of the Mannich base in gasoline fuel detergency since further deposits were reduced or abated after the "dirty-up" step when employed at a 1000 ppm treatment level.

Gasoline ISD Test Results

SwRI® analyzed the above described formulations at 1:1:1 ratios of Mannich product to carrier fluid to Aromatic 150, respectively, using FTM 500.1 test procedures for an Induction System Depository Apparatus (ISD). A blend of Halterman 65th Phillips "J" fuel was used as a base fuel for gasoline testing. "Dirty-up/clean-up" data was provided at 190 C. The formulation based on the Mannich product made with two equivalents of formaldehyde gave results that demonstrates the decrease in deposits from 1.2 mg after dirty-up to 1.0 mg after the clean-up cycle when used at 1000 ppm (wt.-wt.) treatment levels. The three formaldehyde equivalent Mannich product formulation showed a complete abatement of further deposit formation being formed when used at 1000 ppm (wt.-wt.) treatment levels as 1.1 mg dirty-up deposits did not increase after employing the treatment.

All above-mentioned references are hereby incorporated by reference herein.

While the invention has been described with reference to certain aspects or embodiments, it will be understood by those skilled in the art that various changes may be made and equivalents may be substituted for elements thereof without departing from the scope of the invention. In addition, many modifications may be made to adapt the teachings of the invention without departing from the essential scope thereof.

Therefore, it is intended that the invention not be limited to the particular embodiment disclosed as the best mode contemplated for carrying out this invention, but that the invention will include all embodiments falling within the scope of the appended claims.

The invention claimed is:

1. A substituted Mannich base composition comprising a reaction product of (1) an amine component comprising at least one multifunctional amine of structure (I):

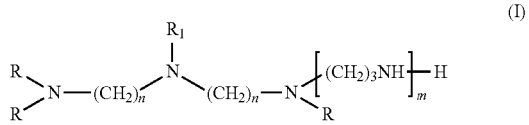

wherein each R is independently H or $CH_2CH_2CH_2NH_2$; $R_1$ is H, $CH_2CH_2CH_2NH_2$, $C_1$-$C_{21}$ alkyl, or $C_2$-$C_{21}$ alkenyl; n is 2; and m is 1 or 2, and (2) an alkyl substituted hydroxyaromatic compound comprising an oligonieric or polymeric alkyl substituent being a polyisobutylene of 250-1500 molecular weight and (3) an aldehyde.

2. The composition of claim 1, wherein the hydroxyaromatic is selected from the group consisting of phenol, o-cresol, and combinations thereof.

3. The composition of claim 1, wherein in which the aldehyde component is an aliphatic or aromatic aldehyde of up to 18 carbons.

4. The composition of claim 3, wherein the aldehyde is formaldehyde or paraformaldehyde.

5. The composition of claim 1, wherein the amine component comprises a compound selected from the group consisting of N-3-aminopropyl diethylenetriamine; N-3-aminopropyl-[N'-3-[N-3-aminopropyl]aminopropyl]diethylenetriamine; N,N'-bis(3-aminopropyl)diethylenetriamine; N,N-bis(3-aminopropyl)diethylenetriamine; N,N,N'-tris(3-aminopropyl)diethylenetriamine; N,N',N''-tris(3-aminopropyl)diethylenetriamine; N,N, N',N'-tetrakis(3-aminopropyl) diethylenetriamine; N,N-bis(3-aminopropyl)-[N'-3-[N-3-aminopropyl]aminopropyl]-[N'-3-aminopropyl] diethylenetriamine; N-3-aminopropyl-[N'-3-[N-3-aminopropyl]aminopropyl]-[N'-3-aminopropyl] diethylenetriamine; and combinations thereof.

6. The composition of claim 1, wherein the amine component comprises a compound wherein R1 is H or $CH_2CH_2CH_2NH_2$.

7. The composition of claim 1, wherein the amine component comprises a mixture of amines of structure according to formula (I) in a parts-by-weight (pbw) ratio of 0 to 50 pbw amine having 4 nitrogen atoms, 40 to 95 pbw amine having 5 nitrogen atoms, and 0 to 50 pbw amine having at least 6 nitrogen atoms.

8. The composition of claim 1, wherein the amine component comprises a mixture of amines of structure according to formula (I) in a parts-by-weight (pbw) ratio of 1 to 15 pbw amine having 4 nitrogen atoms, 50 to 90 pbw amine having 5 nitrogen atoms, and 5 to 35 pbw amine having at least 6 nitrogen atoms.

9. The composition of claim 1, wherein the alkyl substituted hydroxyaromatic component, the aldehyde and amine component are reacted in a ratio of moles of alkyl substituted hydroxyaromatic component to aldehyde to multifunctional amine are from about 0.5-1:0.5-3.5:0.5-2.0.

10. The composition of claim 1, further comprising at least one compound selected from the group consisting of alkyl substituted phenols, dimethylaminomethylphenol, bis(dimethylaminomethyl)phenol, and tris(dimethylaminomethyl)phenol.

11. The composition of claim 1, wherein the composition comprises a reaction product of the amine component, the alkyl substituted hydroxyaromatic component, the aldehyde and at least one additional multifunctional amine having three or more active amine hydrogens or an amine having at least one primary and/or secondary amine as well as at least one tertiary amine.

12. The composition of claim 11, wherein the at least one multifunctional amine is selected from the group consisting of an aliphatic amine, a cycloaliphatic amine, an aromatic amine, a poly(alkylene oxide) diamine or triamine, a Mannich base derivative of an aliphatic amine, a Mannich base derivative of a cycloaliphatic amine, a Mannich base derivative of an aromatic amine, an amine adduct derivative of an aliphatic amine with a glycidyl ether, an amine adduct derivative of a cycloaliphatic amine with a glycidyl ether, or an amine adduct derivative of an aromatic amine with a glycidyl ether, and the like, and combinations thereof.

13. The composition of claim 12, wherein the at least one multifunctional amine is selected from the group consisting of ethylenediamine, diethylenetriamine, triethylenetetramine, tetraethylenepentamine, higher polyethyleneamines, aminoethylpiperazine, meta-xylylenediamine, the various isomers of diamine-cyclohexane, isophorone diamine, 3,3'-dimethyl-4,4'-diaminodicyclohexyl methane, 4,4'-diaminodicyclohexyl methane, 2,4'-diaminodicyclohexyl methane, the mixture of methylene bridged poly(cyclohexyl-aromatic)amines, 1,2-propylenediamine, 1,3-propylenediamine, 1,4-butanediamine, 1,5-pentanediamine, 1,3-pentanediamine, 1,6-hexanediamine, 3,3,5-trimethyl-1,6-hexane-diamine, 3,5,5-trimethyl-1,6-hexanediamine, 2-methyl-1,5-pentanediamine, bis-(3-amino-propyl)amine, N,N'-bis-(3-aminopropyl)-1,2-ethanediamine, N-(3-aminopropyl)-1,2-ethanediamine, 1,2-diaminocyclohexane, 1,3-diaminocyclohexane, 1,4-diamino-cyclohexane, the poly(alkylene oxide)diamines and triamines, aminopropylated ethylene glycols, aminopropylated propanediols, aminopropylated butanediols, aminopropylated hexanediols, aminopropylated polyethylene glycols, aminopropylated polypropylene glycols, aminopropylated polybutanediols, N,N-dimethyl-1,3-propanediamine, N-methyl piperazine, and combinations thereof.

14. A substituted Mannich base fuel additive comprising the composition of claim 1.

15. A fuel composition comprising fuel and the substituted Mannich base fuel additive of claim 14.

16. A method to reduce deposit formation in a fuel system of an internal combustion engine comprising operating the internal combustion system with a fuel according to claim 15.

* * * * *